United States Patent [19]

Meredith

[11] 4,064,881
[45] Dec. 27, 1977

[54] SURGICAL CLIP APPLICATOR

[75] Inventor: Hayden Gwyn Meredith, Kingsbury, England

[73] Assignee: Rocket of London Limited, Watford, England

[21] Appl. No.: 691,324

[22] Filed: June 1, 1976

[30] Foreign Application Priority Data

June 6, 1975 United Kingdom ............... 24374/75

[51] Int. Cl.² ...................... A61B 17/10; A61B 17/12
[52] U.S. Cl. .................................... 128/325; 128/346
[58] Field of Search .................. 128/303 R, 321, 325, 128/346

[56] References Cited

U.S. PATENT DOCUMENTS

| 3,518,993 | 7/1970 | Blake ..................................... 128/321 |
| 3,777,538 | 12/1973 | Weatherly et al. .............. 128/325 X |
| 3,856,016 | 12/1974 | Davis ............................... 128/346 X |
| 3,882,854 | 5/1975 | Hulka et al. ..................... 128/321 X |

Primary Examiner—Channing L. Pace
Attorney, Agent, or Firm—Prutzman, Hayes, Kalb & Chilton

[57] ABSTRACT

An applicator for introducing a surgical sprung clip into a patient's abdomen and setting the clip in position comprises an outer tube having a forward end provided with a clip locating cradle, an inner tube and a pusher rod located in the outer tube for manipulating a clip positioned in the cradle and controls for the inner tube and pusher rod formed as a pistol grip arrangement at the rear end of the outer tube so that an operator can manipulate the applicator controls with one hand.

5 Claims, 6 Drawing Figures

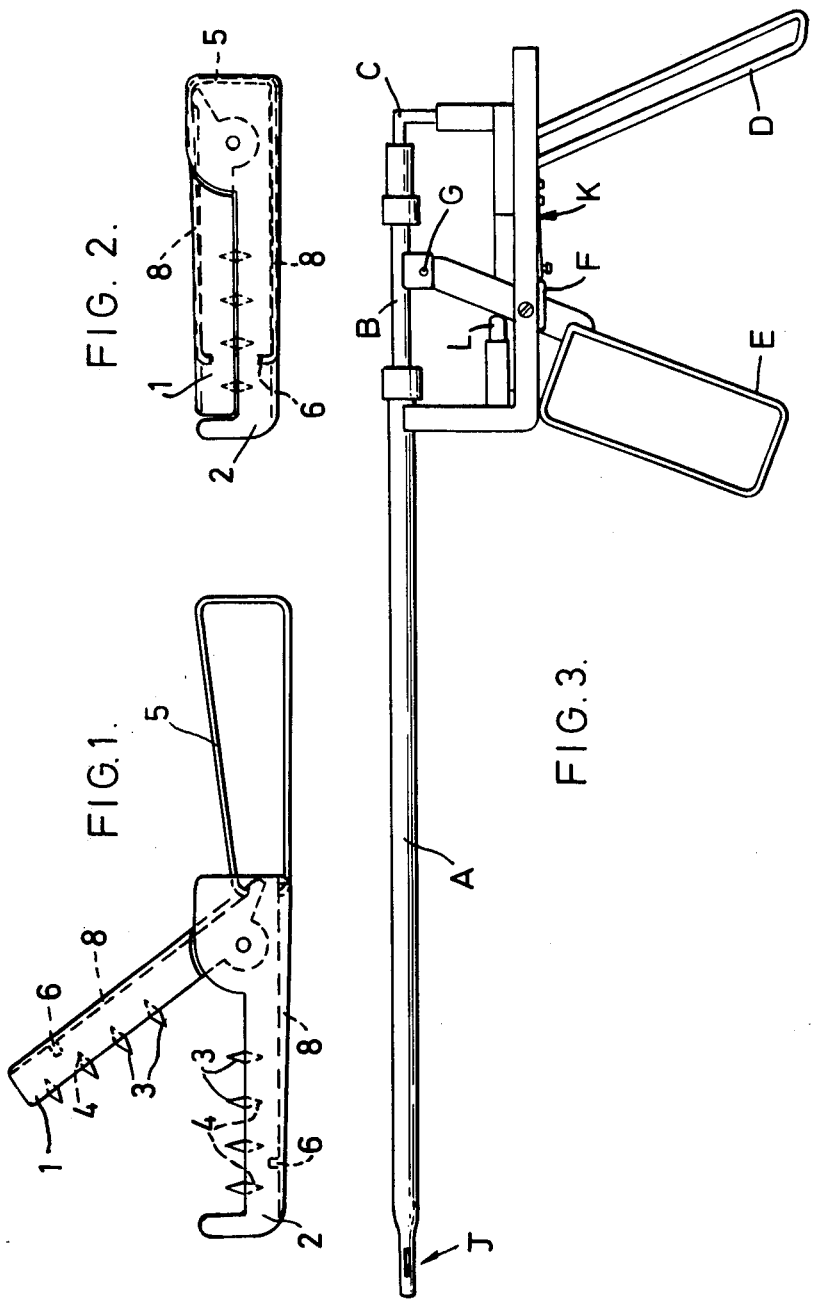

SURGICAL CLIP APPLICATOR

The present invention relates to a device for inserting surgical clips into a human's or animal's body and more particularly to a device for applying clips to occlude the Fallopian tubes.

A particularly useful form of surgical clip for occluding the Fallopian tubes has recently been developed in the United States by Dr. Jaroslav Hulka of The University of North Carolina. This type of clip (hereinafter referred to as a "Hulka" clip) comprises a pair of pivoted synthetic plastics jaws having clamping surfaces provided with complimentary spikes and depressions and a U-shaped gold-plated stainless steel spring which fits over the jaws and which can be slid longitudinally from a first position in which the ends of the spring hold the jaws in an open condition along the outer surfaces of the jaws to a second position in which the ends of the spring (which are turned inwards) engage in recesses near the free ends of the jaws and clamp the jaws in a closed condition against the spring force.

It is an object of the present invention to provide a device capable of inserting a Hulka clip into a patient's body through a suitable cannula and then applying the clip to and clamping the clip on the Fallopian tube.

The invention accordingly provides a surgical clip applicator comprising an outer tube having a forward end and a rear end, a Hulka-type clip-locating cradle formed in the forward end of said outer tube, an inner tube and a pusher rod contained within the outer tube the inner tube having a forward end portion positioned to operate in said cradle to ride along the outer surface of one of the jaws of the clip by relative movement of the tubes to open or close the jaws when the clip spring urges the jaws to an open position, the pusher rod terminating in a forward end portion adapted to act on the spring of a clip in said cradle for pushing the spring from its first to its second position by movement of the pusher rod relative to the outer tube, and independent controls for the inner tube and the pusher rod incorporated in a pistol or revolver-type grip assembly associated with the rear end of the outer tube enabling an operator to hold the device and operate the controls with one hand.

In a preferred form of the invention, the grip assembly includes a butt and pivoted trigger guard arrangement to be gripped between the palm and fingers, the trigger guard forming the control for the inner tube, the butt and trigger guard being mounted on a carriage incorporating a slidable member forming the control for the pusher rod. Preferably, to facilitate manipulation of the clip, the cradle opens into the outer tube from the side of the tube when considered in relation to the grip assembly.

A preferred embodiment of the invention will now to described by way of an example with reference to the accompanying drawings in which:

FIG. 1 is a side view of a Hulka-type surgical clip in an open condition,

FIG. 2 is a side view of the clip in a closed and clamped or locked condition.

FIG. 3 is a view from one side of an applicator for a Hulka-type clip in accordance with the invention.

Figure 4:
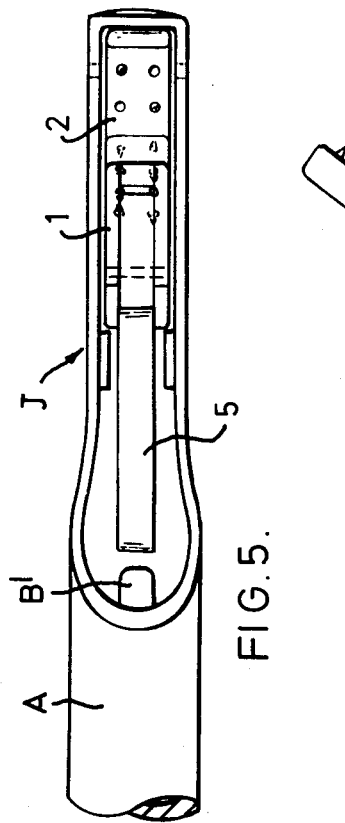
FIG. 4 is a view of the applicator from the other side.

The Hulka-type clip shown in FIGS. 1 and 2 comprises a pair of synthetic plastics pivoted jaws 1 and 2 the clamping surfaces of which are formed with complimentary spikes and depressions 3 and 4. In FIG. 1 the clip is shown being held in an open condition by an associated gold-plated U-shaped stainless steel spring 5. To close and lock the clip (FIG. 2) the free ends of the spring (turned inwardly as shown) are slid along slots 8 in the outer surfaces of the jaws until the free ends engage in recesses 6 provided in the respective jaws.

To introduce a clip into a patient's abdomen through a previously inserted cannula, a clip applicator as shown in FIGS. 3 to 6 is used. The applicator consists of an outer tube A terminating at its forward end in a clip-retaining cradle J opening from the side of the tube and dimensioned so as positively to locate a clip between front and rear cradle abutments as seen most clearly in FIG. 5, the clip being shown with the spring 5 extending rearwardly along the outer tube between the rear cradle abutments. An inner tube B is situated within the outer tube and has a forward end B' located to ride over the upper clip jaw to open or close the jaw when the clip is urged by its spring into an open condition. Extending through the inner tube is a pusher rod C having a forward end for pushing against the spring 5 to move the spring from its position as shown in FIG. 1 to its position as shown in FIG. 2.

Figure 5:
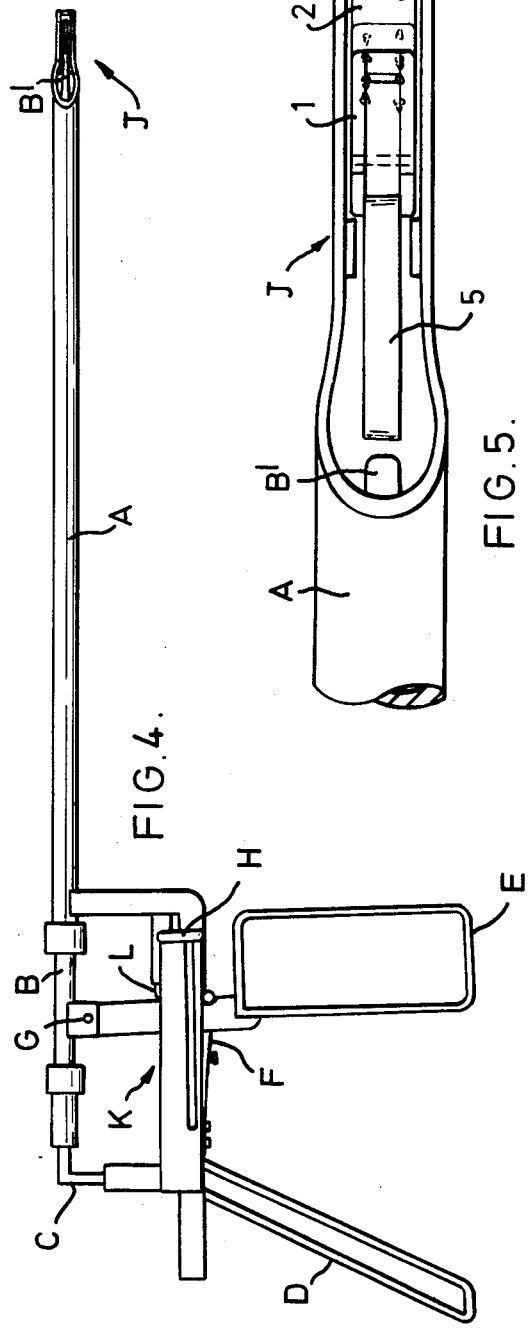
FIG. 5 is a side view to an enlarged scale of the forward end of the applicator showing a Hulka-type clip located in a cradle portion of the applicator.
Figure 6:
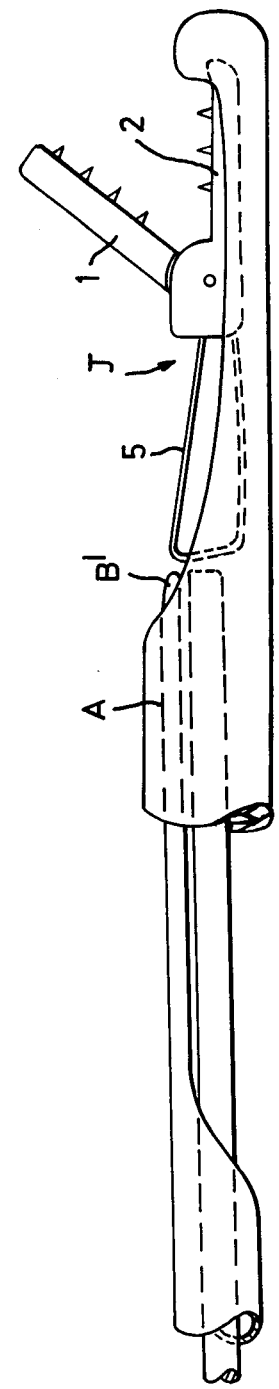
FIG. 6 is a plan view corresponding to FIG. 5.

At its rear end, the outer tube is attached to a carriage K having a depending fixed butt D and a pivoted trigger guard E forming a control for moving the inner tube B within the outer tube. The butt and trigger guard can be gripped between the palm and fingers to form, with the carriage K a pistol or revolver type grip assembly. The trigger guard is urged by a spring button L towards the position shown in FIG. 3 in which the forward end of tube B is withdrawn from the clip (as shown in FIGS. 5 and 6) but the guard is normally held against the spring in the position shown in FIG. 4 by a press-down latch F on the carriage which engages in a detent in the trigger guard. The carriage also has a sliding latch H forming a control for moving the pusher rod C relative to the inner tube.

Loading the clip into the cradle is accomplished by releasing the press-down latch F so that the trigger guard E moves forward under the spring action (FIG. 3). This has the effect at the distal end of withdrawing the inner tube B and pusher C exposing the cradle to receive the lower half of the clip. Returning the trigger guard E to its normal position (FIG. 4) moves a pivot location G formed on the inner tube forward so that the forward end of the inner tube moves into the slot 8 in the top surface of the clip thus ensuring that complete sideways location as accomplished. This prevents accidental loss of the clip during introduction. The applicator and clip are then ready for use.

The clip is closed by squeezing the trigger guard during insertion of the instrument and clip through a cannula passed through the abdominal wall to move the forward end of the inner tube forwardly along the open clip jaw. When free abdominal space is reached, releasing the trigger guard E opens the clip to allow clamping of the patient's Fallopian tube. The clip may be opened and closed again at will by squeezing the trigger guard E. This facility for easy opening and closing of the clip allows for possible resighting of the clip position along the Fallopian tube before irreversible positioning. Its optimum position is determined by laparoscopic inspection.

When the correct position has been determined the clip can be finally secured in position by releasing the latch F controlling a stop (not shown) for the sliding latch H and then advancing the latch H. This moves the pusher rod C forward and in turn closes the gold plated stainless steel spring 5 onto the locking position on the clip. Withdrawing the instrument can now be accomplished by opening the trigger guard E by depressing the latch F (FIG. 3) to open the instrument to its maximum apertures.

For dismantling, the sliding pusher rod C may be removed from the frame by depressing a rear detent pin (not shown) located in the sliding tracks at the bottom of the frame. This item also serves as a back stop to limit frame movement. The inner tube B may then be removed completely, by depressing the latch F to allow withdrawal of the inner sleeve.

I claim:

1. In a hand operated surgical clip applicator for positioning and actuating a jaw-like surgical clip and clamping an associated spring thereon comprising an elongated positioning tube having a cradle at one end thereof for holding said clip and spring and independent actuating and clamping controls at the opposite end thereof, a first actuating member slidably mounted within said tube for actuating said jaw-like clip and an independent second actuating member slidably mounted within said tube for clamping said associated spring on said clip, said independent actuating and clamping controls controlling slidable movement of said actuating members, the improvement wherein said controls are of a pistol grip assembly configuration adapted for operation by only one hand of an operator comprising a stationary elongated carriage member depending from said tube in fixed, spaced, substantially parallel relationship thereto and supporting a fixed gripping butt thereon, a trigger member pivotally mounted on said carriage for movement toward and away from said butt and connected to said first actuating member for controlling sliding movement of said first actuating member toward and away from said cradle, and a slide lever slidably mounted on said carriage member for reciprocal sliding movement therealong and connected to said second actuating member for independently slidably moving said second member along said tube as said slide lever slides along said carriage member, said slide lever including a laterally extending actuating portion adapted for actuation by the same hand of the operator gripping said butt and trigger members.

2. The applicator of claim 1 wherein said first actuating member comprises an actuating tube having a forward end portion configured to ride over said spring and clip positioned within said cradle for actuating said clip, said second actuating member being slidably mounted within said actuating tube for independent movement into driving engagement with said spring to drive said spring into clamping engagement with said clip.

3. The applicator of claim 1 wherein said surgical clip moves between open and closed positions, one end of said first actuating member being positioned at said cradle, said first member being slidably movable between a fully withdrawn position with said one end free from engagement with said clip and spring and a fully actuated position with said one end holding said clip in its closed position.

4. The applicator of claim 3 wherein said first actuating member is movable into and out of a position intermediate said fully withdrawn and fully actuated positions with said one end thereof engaging said clip in its open position to prevent displacement of the clip from the cradle, spring means urging said first actuating member toward its fully withdrawn position and latching means latching said first actuating member in said intermediate position against the bias of said spring means.

5. An applicator as claimed in claim 1 wherein the cradle opens into the outer tube from the side of the tube when considered in relation to the grip assembly.

* * * * *